(12) United States Patent
Anderson

(10) Patent No.: US 12,274,763 B2
(45) Date of Patent: Apr. 15, 2025

(54) CATECHOL-CONTAINING MATERIAL FOR USE IN DENTAL APPLICATIONS

(71) Applicant: Mussel Polymers, Inc., Bethlehem, PA (US)

(72) Inventor: Eric Anderson, Princeton, NJ (US)

(73) Assignee: Mussel Polymers, Inc, Bethlehem, PA (US)

( * ) Notice: Subject to any disclaimer, the term of this patent is extended or adjusted under 35 U.S.C. 154(b) by 184 days.

(21) Appl. No.: 17/933,809

(22) Filed: Sep. 20, 2022

(65) Prior Publication Data

US 2023/0092416 A1 Mar. 23, 2023

Related U.S. Application Data

(60) Provisional application No. 63/287,124, filed on Dec. 8, 2021, provisional application No. 63/245,959, filed on Sep. 20, 2021.

(51) Int. Cl.
| | |
|---|---|
| *A61K 6/30* | (2020.01) |
| *A61K 6/60* | (2020.01) |
| *A61K 6/62* | (2020.01) |
| *A61K 6/802* | (2020.01) |
| *A61K 6/818* | (2020.01) |
| *A61K 6/889* | (2020.01) |
| *C09J 133/10* | (2006.01) |

(52) U.S. Cl.
CPC .............. *A61K 6/30* (2020.01); *A61K 6/60* (2020.01); *A61K 6/62* (2020.01); *A61K 6/802* (2020.01); *A61K 6/818* (2020.01); *A61K 6/889* (2020.01); *C09J 133/10* (2013.01)

(58) Field of Classification Search
CPC .. F16N 29/04; A61C 5/00; A61K 6/20; A61K 6/30; A61K 6/40; A61K 6/60; A61K 6/62; A61K 6/802; A61K 6/818; A61K 6/889; C08F 12/24; C08L 33/08; C08L 33/10; C09D 125/18; C09J 133/10
See application file for complete search history.

(56) References Cited

U.S. PATENT DOCUMENTS 6,506,577 B1 * 1/2003 Deming ............... C07K 14/001
530/211

OTHER PUBLICATIONS

Cheng et al. 2022—Ultrastrong underwater adhesion on diverse substrates using non-canonical phenolic groups, Nature Communications.

(Continued)

*Primary Examiner* — Lawrence D Ferguson
(74) *Attorney, Agent, or Firm* — BakerHostetler

(57) ABSTRACT

The present disclosure is directed to a polymeric layer comprising a catechol containing a monomer, polymer, or oligomer, wherein said catechol presents as a catechol and/or as a semi-quinone and/or as a quinone without the presence of a primary amine or a secondary amine; and wherein the polymeric layer optionally comprises a reactive material that is not reactive with catechol or quinone. The present disclosure is also directed to a polymeric layer comprising a catechol containing monomer, polymer, or oligomer disposed adjacent to and in contact with a bulk adhesive layer. The present disclosure is also directed to methods of coating a substrate using the layers described herein.

18 Claims, 12 Drawing Sheets

(56) References Cited

OTHER PUBLICATIONS

Guvendiren, M., Brass, D. A., Messersmith, P. B. & Shull, K. R. Adhesion of DOPA-Functionalized Model Membranes to Hard and Soft Surfaces. J. Adhes. 85, 631-645 (2009).

LaVoie, M. J., Ostaszewski, B. L., Weihofen, A., Schlossmacher, M. G. & Selkoe, D. J. Dopamine covalently modifies and functionally inactivates parkin. Nat. Med. 11, 1214-1221 (2005).

Burzio, L. A. & Waite, J. H. Cross-linking in adhesive quinoproteins: Studies with model decapeptides. Biochemistry 39, (2000).

Mutluay, M. M. et al. Fatigue of the resin-dentin interface: a new approach for evaluating the durability of dentin bonds. Dent. Mater. 29, 437-449 (2013).

Arola, D. Fatigue testing of biomaterials and their interfaces. Dent. Mater. 33, 367-381 (2017).

Montoya, C. et al. Multifunctional Dental Composite with Piezo-electric Nanofillers for Combined Antibacterial and Mineralization Effects. ACS Appl. Mater. Interfaces 13, 43868-43879 (2021).

* cited by examiner

- Dentin is a spongy, wet tissue
- Acrylic adhesives display poor wet bonding
- Acid etching, priming used
- Most adhesion is mechanical ("resin tags")
- Resin tags fail over time
- Filling failure in <7 years 60% of filling procedures are to replace old, failed fillings

CATECHOL-CONTAINING MATERIAL FOR USE IN DENTAL APPLICATIONS

CROSS REFERENCE TO RELATED APPLICATIONS

This application claims the benefit of U.S. Provisional Application No. 63/245,959, filed Sep. 20, 2021, and U.S. Provisional Application No. 63/287,124, filed Dec. 8, 2021, the entirety of which are incorporated by reference herein.

TECHNICAL FIELD

The present disclosure relates to thin layers comprising a catechol containing monomer, polymer, or oligomer for use in dental applications. Catechol containing materials demonstrate improved adhesion between two materials without substantial modification of the adhesive matrix. The present disclosure also relates to methods of making and using the thin layers comprising a catechol containing polymer or oligomer, Poly(Catechol-Styrene) (PCS).

BACKGROUND

Strong, durable adhesion between tooth surfaces and composite filling materials, orthodontic devices, and restorative ceramics is a longstanding, challenging, and costly problem in the field of dentistry with implications for health, safety, and welfare. Dental adhesives must bind strongly to wet tooth surfaces and maintain strength in the wet oral environment. Formulated acrylic resins are the most commonly used adhesive chemistry in dentistry. These resins are applied in their liquid monomeric form and polymerized in situ. Polymerization of acrylic resins is frequently light activated, although some self-polymerization chemistries are also used.

Because acrylic adhesives bind poorly to wet surfaces, surfaces on the patient's teeth are usually first etched with phosphoric-acid and air-dried. To enhance further binding strengths, some substrates are also treated with primers. For ease of applications, some dentists often use multi-part adhesive systems composed of combinations of etchant, adhesive, and primer in a single formulation. At application, most of the strength of this bond comes from micromechanical interlocking. While chemical bonding between the dental adhesive and the tooth structure is relatively limited, some studies suggest they are largely responsible for determining bond longevity.

However, even when initial adhesive attachments are strong, acrylic adhesives lose bonding strength steadily over time. The progressive loss of bonding strength has been heavily studied and has been found to be the result of several factors, such as hydrolysis of the acrylic adhesives, degradation of dentin collagen by activated matrix metalloproteases, and poor initial adhesion of the acrylic to the wet dentin and enamel.

In addition, hydroxyapatite removal by etching permanently compromises the tooth enamel, increasing the likelihood of future caries. Liquid etchant may flow to the gingiva, irritating the tissue. Some patients may have an allergic reaction to the etchant. Accordingly, a need exists for the successful use of catechol containing materials to improve bonding strength and longevity of dental adhesives in the wet conditions of the oral cavity.

SUMMARY OF THE INVENTION

In certain aspects, the present invention relates to a polymeric layer comprising a catechol-containing thin-film comprised of a polymer containing catechol, semi-quinone, or quinone to enhance the binding strength of a dental adhesive.

In some embodiments, the catechol-containing thin-film comprises monomeric, oligomeric, or polymeric catechol or catechol containing material, wherein said catechol presents as a catechol and/or as a semi-quinone and/or as a quinone without the presence of an amine; and wherein the polymeric layer optionally comprises at least one of: a) a reactive species separate from the catechol or catechol containing material; and b) a catalyst, co-catalyst or an accelerator.

In some embodiments, the polymeric layer comprises the reactive species separate from the catechol or catechol containing material; and the reactive species comprises an acrylic, a silane, a silicone, a methacrylate, a polyvinyl alcohol (PVA) or a combination thereof.

In some embodiments the polymeric layer comprises the reactive species separate from the catechol or catechol containing material; and the reactive species is an acrylic such as 2,2-bis[4-(2-hydroxy-3-methacryloyloxypropoxy)phenyl]propane (BisGMA), ethoxylated bisphenol-A dimethacrylate (EBPADMA), triethylene glycol dimethacrylate (TEGDMA), urethane dimethacrylate (UDMA), tert-butylphenoxy BisGMA (MtBDMA), modified urethane dimethacrylate, amide modified bisphenol-A, $CH_3BisGMA$, acidic bisphenol-A dimethacrylate, dimethacrylate from cycloaliphatic epoxide, aromatic urethane dimethacrylate, urethane modified BisGMA, acid aromatic dimethacrylate, oxydiphthalic-acid dimethacrylate, phenyl dihydroxymethacrylate diphosphonate, Acidic Bisphenol-A dimethacrylate, morpholine carbonyl methacrylate, phenyl carbonate methacrylate.

In some embodiments, the invention as contemplated herein further comprises free radical polymerization initiators such as acrylate polymerization initiators, including those that are light activated, such as benzoyl peroxide (BPO), 2,3-bornanedione (Camphorquinone), Ethyl-4-(dimethylamino)benzoate (EDMAB), 2-(Ethylhexyl)-4-(dimethylamino)benzoate (ODMAB), 2-(Ethylhexyl)-4-(dimethylamino)benzoate (TPO), Diphenyl(2,4,6-trimethylbenzoyl)-phosphineoxide or combinations thereof.

In some embodiments, the reactive species is the acrylate.

In some embodiments, the polymeric layer is disposed upon a dental substrate. In some embodiments, the dental substrate comprises one or more of a ceramic, a polymer, a composite and a metal. In some embodiments, the ceramic comprises zirconia or porcelain; the polymer comprises acrylic, polypropylene, poly(methyl methacrylate), or one or more combinations thereof, the composite comprises one or more of enamel, dentin, or combinations thereof; and the metal comprises one or more of titanium, stainless steel, gold, chrome, or one or more combinations thereof.

In some embodiments, the polymeric layer comprises one or more of a primer layer, an adhesive layer, or a layered restoration. In some embodiments, the polymeric layer has a thickness of from about 10 nanometers to about 500 microns. In some embodiments, the catechol or catechol-containing material comprises poly-catechol styrene (PCS). In some embodiments, the PCS comprises a 0.1% solution of PCS.

In some embodiments, the invention as contemplated herein further comprises one or more photo-initiators comprising one or more of camphorquinone (CQ), azobisisobutyronitrile (AIBN), benzoyl peroxide, 2,2-dimethoxy-2-phenylacetophenone, and one or more combinations thereof. In some embodiments, the binding longevity of the dental adhesive is improved over dental adhesives not containing a catechol-containing material.

In certain aspects, the present invention provides a method of coating a substrate comprising disposing the polymeric layer of claim 1 on a surface of the substrate.

In some embodiments, the substrate comprises a dental substrate comprising one or more of a ceramic, a polymer, a composite and a metal, wherein: the ceramic comprises zirconia or porcelain; the polymer comprises acrylic, polypropylene, poly(methyl methacrylate), or one or more combinations thereof, the composite comprises one or more of enamel, dentin, or combinations thereof, and the metal comprises one or more of titanium, stainless steel, gold, chrome, or one or more combinations thereof.

In some embodiments of the method the substrate is wet, dry, semi-wet or moist. In some embodiments of the method the substrate is inside the oral cavity of a subject. In some embodiments, the binding longevity of the dental adhesive is improved over dental adhesives not containing a catechol-containing material.

DETAILED DESCRIPTION OF ILLUSTRATIVE EMBODIMENTS

Figure 1:
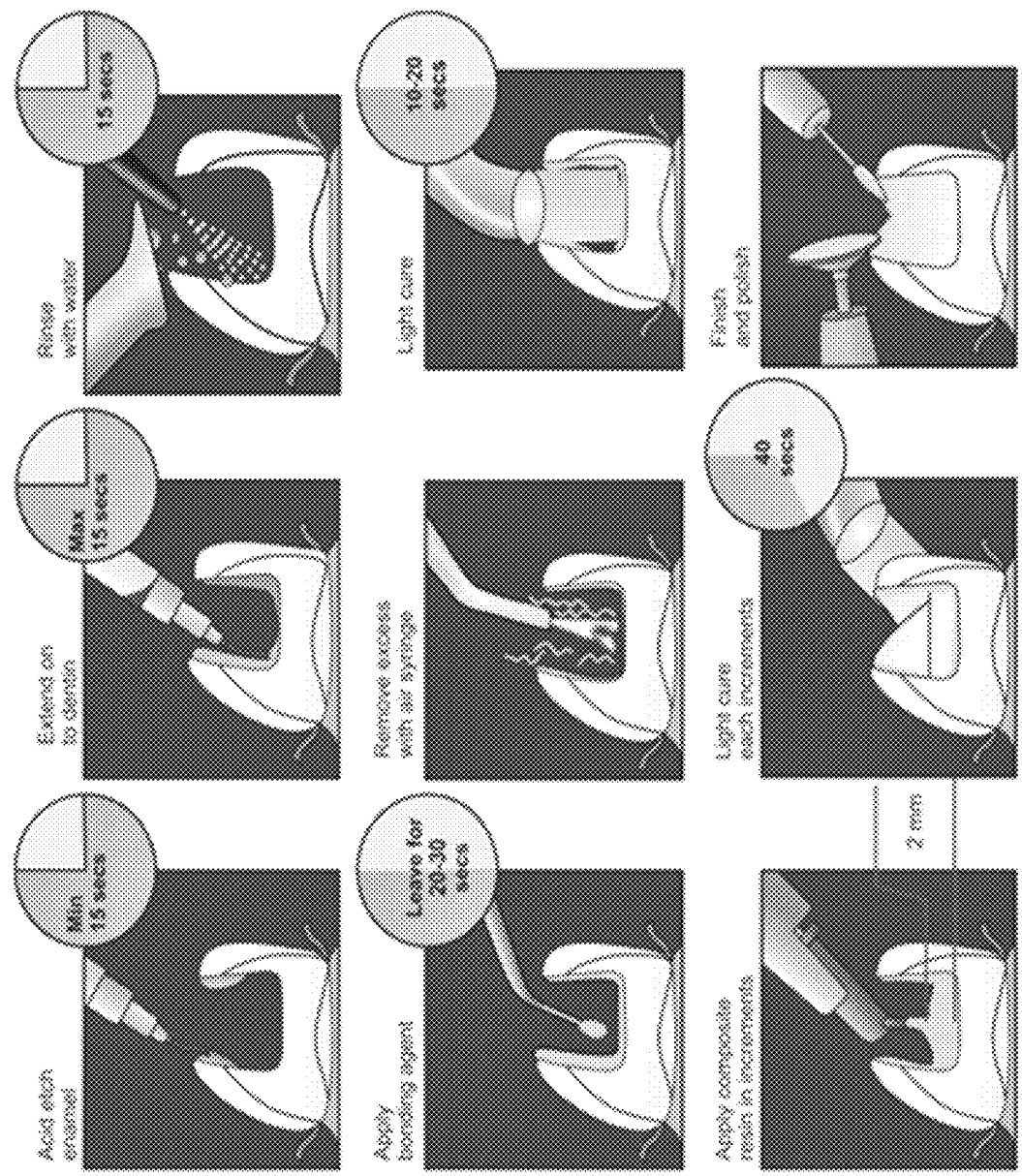
FIG. 1 depicts a schematic of an exemplary procedure for placing dental restorations using composite fillings. The schematic, obtained from Jain, A. 2016, depicts an exemplary technique for placing a light-cured composite restoration.
Figure 2:
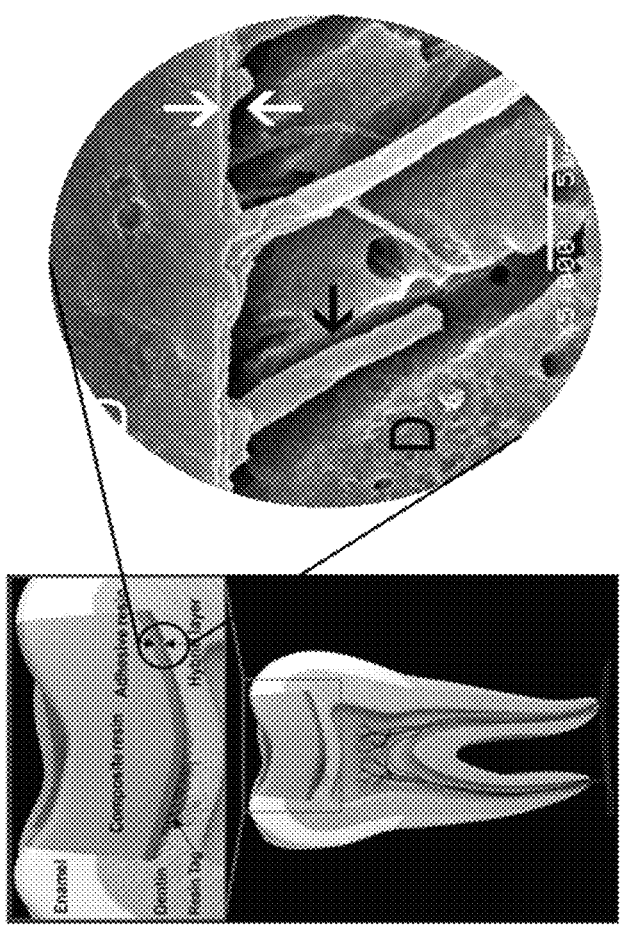
FIG. 2 is a schematic showing the attachment of composite fillings.
Figure 3:
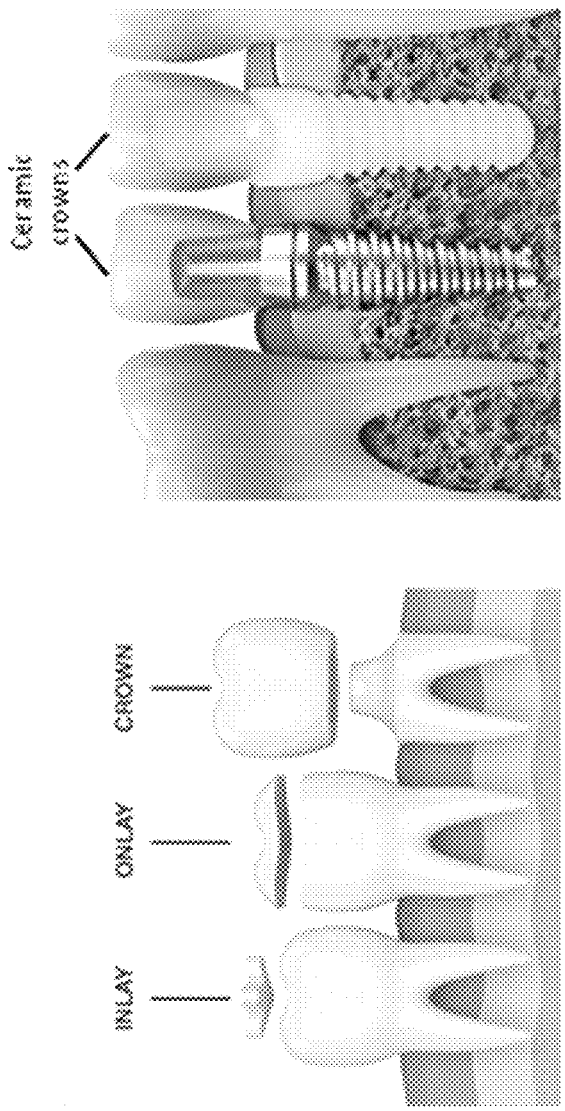
FIG. 3 is a schematic demonstrating the use of ceramics for bridgework and dental implants.

In the present disclosure the singular forms "a", "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

In the present disclosure, the term "subject" includes any human or non-human animal. In certain embodiments, the subject is a human or non-human mammal. In certain embodiments, the subject is a human.

When a value is expressed as an approximation by use of the descriptor "about" or "substantially" it will be understood that the particular value forms another embodiment. In general, use of the term "about" or "substantially" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about" or "substantially". In other cases, the gradations used in a series of values may be used to determine the intended range available to the term "about" or "substantially" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

It is to be appreciated that certain features of the disclosure which are, for clarity, described herein in the context of separate embodiments, may also be provided in combination in a single embodiment. That is, unless obviously incompatible or excluded, each individual embodiment is deemed to be combinable with any other embodiments and such a combination is considered to be another embodiment. Conversely, various features of the disclosure that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

Marine mussel adhesive proteins have attracted considerable research interest due at least in part to their strong adhesion to a wide range of substrates in the presence of water.

Figure 4:
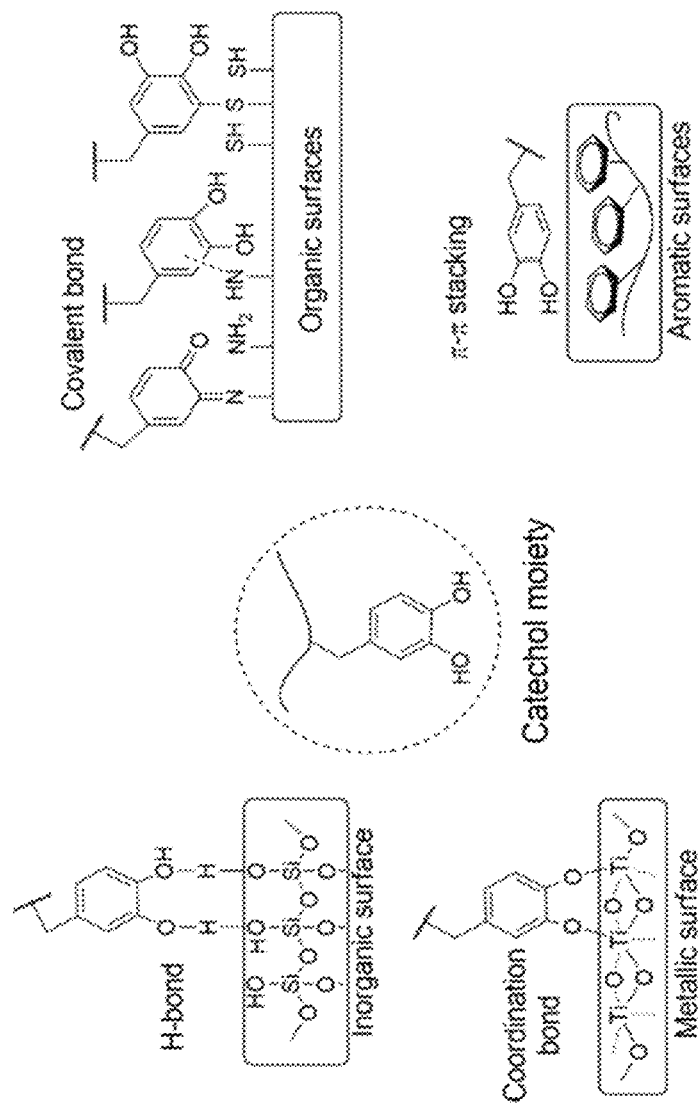
FIG. 4 is a schematic of exemplary interactions of catechols with different types of surfaces.
Figure 5:
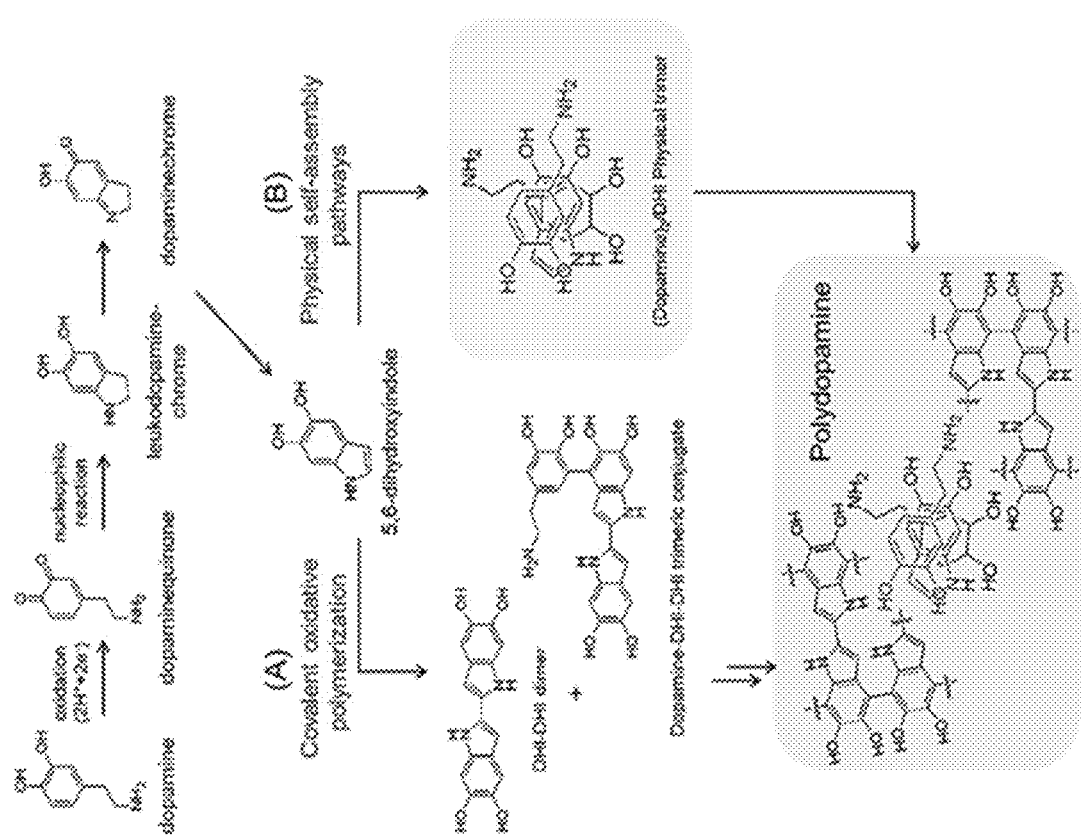
FIG. 5 is a schematic demonstrating the auto-polymerization and structure of polydopamine.

Mussels secrete mussel foot proteins (Mfps), which enables them to adhere onto various surfaces (e.g., rock, wood, metallic surface, sea creature shell, etc.) in a wet environment. One of the key constituents of Mfps is a relatively large amount of the rare amino acid 3,4-dihydroxy-1-phenylalanine (DOPA). DOPA contains a catechol side chain, and this catechol group has been shown to be primarily responsible for the remarkable adhesive properties of the Mfps. Catechol is able to form a wide range of reversible bonds with surfaces, such as hydrogen bonding, cation-π interaction, and metal ion complexation. Catechol can also form covalent bonds with certain bonding surfaces, for example protein surfaces, as well as cross-linking with itself. (FIG. 4)

An understanding of this remarkable catechol chemistry has inspired the development of catechol-containing bioadhesives and biomaterials, which can be used for a wide range of applications.

Catechol groups are susceptible to oxidation into a semi-quinone or quinone. Several studies have documented that oxidation reduces significantly binding to inorganic surfaces. During the process of catechol oxidation into quinones, reactive oxygen species (ROS) are generated as by-products.

While strong attachment to inorganic surfaces requires catechol (reduced), quinones (oxidized) can bind covalently to organic materials via a Schiff base addition or Michael Reaction. Mussel-inspired biomimetic adhesives can be considered bifunctional "catechol-quinone" mixtures.

Catechol containing materials of the present invention can be used as a primer, an adhesive, a sealant, or a restoration material for a tooth or other dental substrate. The catechol containing materials may be used as an adhesive, part of a restorative material for a restoration, a sealant, or the like. The catechol containing materials may be used with one or more dental material including, for example, one or more of commercially available adhesives, fillings, or the like, to improve the adhesion or performance of the dental material. The catechol containing material may be used, for example as a primer. In some embodiments, the dental substrate includes dental implants such as synthetic teeth having a ceramic surface or the like (e.g., zirconia or porcelain), tooth substrates including natural tooth substrates (e.g., enamel, dentin or a combination of the two), fixed orthodontic devices including orthodontic brackets (e.g., titanium, stainless steel, gold, chrome, polypropylene, acrylic, poly(methyl methacrylate) (PMMA), or other suitable material), and/or ceramic restorative devices (e.g., zirconia crowns, etc.).

Figure 6:
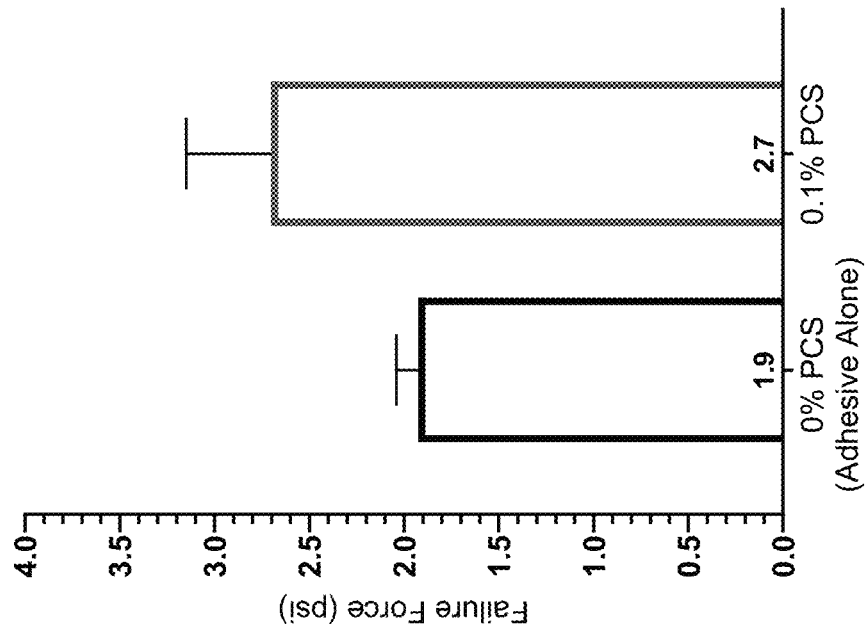
FIG. 6 demonstrates that Poly(Catechol-Styrene) (PCS) priming enamel promotes dental bracket bonding with a dental acrylic. Priming (0.1% PCS in acetone) improves bonding of a bracket to an enamel surface using a universal self-etch dental adhesive (Henry Schein Natural Elegance Universal One). Samples were cured for 48 hours. in water before measuring the force required to displace the bracket. Error bars are standard error of the mean.
Figure 6:
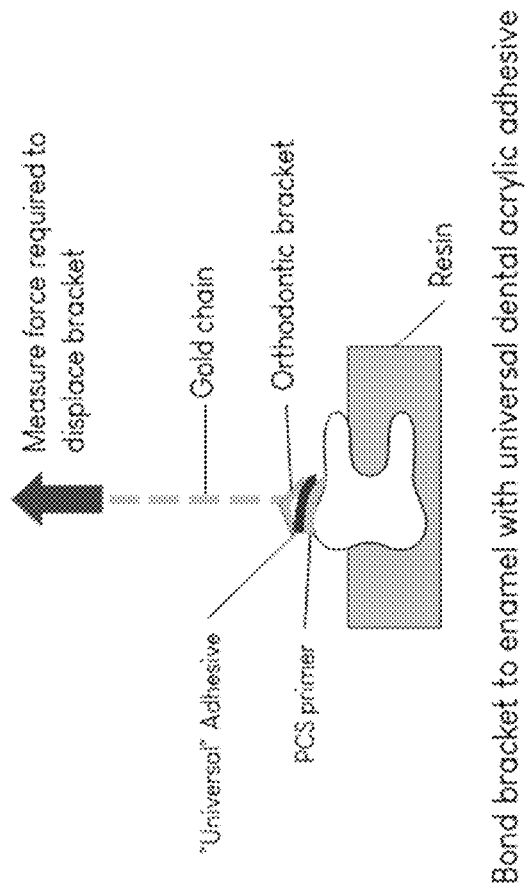

In an aspect, the disclosure is directed to a polymeric layer, shown as the PCS primer layer in FIG. 6, comprising a catechol containing monomer, polymer, or oligomer, wherein said catechol presents as a catechol and/or as a semi-quinone and/or as a quinone without the presence of a primary amine or a secondary amine; and wherein the polymeric layer also comprises a reactive material that is not reactive with catechol or quinone.

In an aspect, the present invention is directed to a polymeric layer, shown as the PCS primer layer in FIG. 6, comprising a catechol containing monomer, polymer, or oligomer, wherein said catechol presents as a catechol and/or as a semi-quinone and/or as a quinone without the presence of a primary amine or a secondary amine; and wherein the polymeric layer optionally comprises a reactive material that is not reactive with catechol or quinone; and wherein the polymeric layer further comprises a bulk adhesive layer, shown as the universal adhesive layer in FIG. 6, disposed adjacent to and in contact with the polymeric layer.

In an aspect, the disclosure is directed to a polymeric layer comprising a catechol containing monomer, polymer, or oligomer, wherein said catechol presents as a catechol and/or as a semi-quinone and/or as a quinone without the presence of a primary amine or a secondary amine; and wherein the polymeric layer also comprises a reactive material that is not reactive with catechol or quinone; and wherein the polymeric layer further comprises a bulk adhesive layer disposed adjacent to and in contact with the polymeric layer.

FIG. 6 depicts a general schematic of an embodiment of the polymeric layer comprising the catechol containing monomer, polymer, or oligomer and a layered article comprising the polymeric layer described herein. The layered article may comprise a substrate which the polymeric layer is disposed on and in contact with. The layered article may also comprise a bulk adhesive layer disposed on the polymeric layer and in contact with the polymeric layer.

In some embodiments, the catechol containing monomer, polymer, or oligomer in the polymeric layer is monomeric. In some embodiments, the catechol containing monomer, polymer, or oligomer in the polymeric layer is oligomeric. In some embodiments, the catechol containing monomer, polymer, or oligomer in the polymeric layer is polymeric.

In some embodiments, the polymeric layer comprises the reactive species separate from the catechol or catechol containing material; and the reactive species is an acrylic such as 2,2-bis[4-(2-hydroxy-3-methacryloyloxypropoxy) phenyl]propane (BisGMA), ethoxylated bisphenol-A dimethacrylate (EBPADMA), triethylene glycol dimethacrylate (TEGDMA), urethane dimethacrylate (UDMA), tert-butylphenoxy BisGMA (MtBDMA), modified urethane dimethacrylate, amide modified bisphenol-A, $CH_3BisGMA$, acidic bisphenol-A dimethacrylate, dimethacrylate from cycloaliphatic epoxide, aromatic urethane dimethacrylate, urethane modified BisGMA, acid aromatic dimethacrylate, oxydiphthalic-acid dimethacrylate, phenyl dihydroxymethacrylate diphosphonate, Acidic Bisphenol-A dimethacrylate, morpholine carbonyl methacrylate, phenyl carbonate methacrylate.

In some embodiments, the polymeric layer includes free radical polymerization initiators such as acrylate polymerization initiators, including those that are light activated, such as benzoyl peroxide (BPO), 2,3-bornanedione (Camphorquinone), Ethyl-4-(dimethylamino)benzoate (EDMAB), 2-(Ethylhexyl)-4-(dimethylamino)benzoate (ODMAB), 2-(Ethylhexyl)-4-(dimethylamino)benzoate (TPO), Diphenyl(2,4,6-trimethylbenzoyl)-phosphineoxide or combinations thereof.

In some embodiments, the acrylate is an acrylate monomer comprising a vinyl group and at least one of a carboxylic acid ester and a carboxylic acid nitrile; and wherein the acrylate is linear or branched. In some embodiments, the acrylate is ethyl acrylate, ethylene-methyl acrylate, methyl methacrylate, 2-chloroethyl vinyl ether, 2-hydroxyethyl acrylate, hydroxyethyl methacrylate, butyl acrylate, trimethylolpropane triacrylate (TMPTA) or combinations thereof.

In an aspect, the polymeric layer has a thickness of from about 10 nanometers to about 100 microns. In some embodiments, the polymeric layer has a thickness of from about 15 nanometers to about 50 microns. In some embodiments, the polymeric layer has a thickness of from about 15 nanometers to about 15 microns. In some embodiments, the polymeric layer has a thickness of from about 150 nanometers to less than about 15 microns. In some embodiments, the polymeric layer has a thickness of from about 150 nanometers to about 1.5 microns.

In some embodiments, the polymeric layer has a thickness of from about 10 nanometers to about 100 microns; or from about 10 nanometers to about 100 nanometers; or from about 100 nanometers to about 150 nanometers; or from about 150 nanometers to about 200 nanometers; or from about 200 nanometers to about 250 nanometers; or from about 250 nanometers to about 300 nanometers; or from about 300 nanometers to about 350 nanometers; or from about 350 nanometers to about 400 nanometers; or from about 400 nanometers to about 450 nanometers; or from about 450 nanometers to about 500 nanometers; or from about 500 nanometers to about 550 nanometers; or from about 550 nanometers to about 600 nanometers; or from about 600 nanometers to about 650 nanometers; or from about 650 nanometers to about 700 nanometers; or from about 700 nanometers to about 750 nanometers; or from about 750 nanometers to about 800 nanometers; or from about 800 nanometers to about 850 nanometers; or from about 850 nanometers to about 900 nanometers; or from about 900 nanometers to about 950 nanometers; or from about 950 nanometers to about 1000 nanometers.

In some embodiments, the polymeric layer has a thickness of from about 1 micron to about 1.5 microns; or from about 1.5 microns to about 5 microns; or from about 5 microns to about 10 microns; or from about 10 microns to about 15 microns; or from about 15 microns to about 20 microns; or from about 20 microns to about 25 microns; or from about 25 microns to about 30 microns; or from about 30 microns to about 35 microns; or from about 35 microns to about 40 microns; or from about 40 microns to about 45 microns; or from about 45 microns to about 50 microns; or from about 50 microns to about 55 microns; or from about 55 microns to about 60 microns; or from about 60 microns to about 65 microns; or from about 65 microns to about 70 microns; or from about 70 microns to about 75 microns; or from about 75 microns to about 80 microns; or from about 80 microns to about 85 microns; or from about 85 microns to about 90 microns; or from about 90 microns to about 95 microns; or from about 95 microns to about 100 microns.

In an aspect, the catechol containing monomer, polymer, or oligomer in the polymeric layer comprises poly-catechol styrene (PCS).

In some embodiments, the PCS is prepared in one or more suitable solvents. For example, the PCS may be prepared as a solution in acetone, tert-butyl alcohol, ethanol, isopropyl alcohol, or a combination thereof, or one or more other suitable solvents as understood in the art. In some embodiments, the PCS is prepared as a solution in acetone. In some embodiments, the PCS is prepared as a solution in tert-butyl alcohol. In some embodiments, the PCS is prepared as a solution in isopropyl alcohol. In some embodiments the PCS is prepared as a solution in ethanol.

In some embodiments, the PCS comprises a solution containing from about 0.001% to 10% PCS, from about 0.05% to about 5% PCS, from about 0.01% to about 2% PCS, from about 0.5% to about 1% PCS, from about 0.1% to about 0.5% PCS and any and all increments therebetween. In some embodiments, the PCS comprises about 0.1% catechol.

In some embodiments, the PCS comprises from about 20% catechol to about 22% catechol; or from about 22% catechol to about 24% catechol; or from about 24% catechol to about 26% catechol; or from about 26% catechol to about 28% catechol; or from about 28% catechol to about 30% catechol; or from about 30% catechol to about 32% catechol; or from about 32% catechol to about 34% catechol; or from about 34% catechol to about 36% catechol; or from about 36% catechol to about 38% catechol; or from about 38% catechol to about 40% catechol.

In some embodiments, the polymeric layer comprises a reactive material that is not reactive with catechol or quinone. In some embodiments, the reactive material is not reactive at ambient temperature with catechol or quinone. In some embodiments, the reactive material is not reactive at low temperature with catechol or quinone.

In some embodiments, the reactive material that is not reactive with catechol or quinone is a resin, an oligomer, a polymer, or a monomer. In some embodiments, the reactive material an oligomer. In some embodiments, the reactive material a polymer. In some embodiments, the reactive material a monomer.

In an aspect, the polymeric layer is a continuous layer. In an aspect, the polymeric layer is a non-continuous layer. In an aspect, the polymeric layer is a patterned layer or a textured layer.

In some embodiments, the polymeric layer includes one or more additives. In some embodiments, the one or more additives include one or more catalysts, for example one or more photo-initiators. The one or more photo-initiators may include one or more of camphorquinone (CQ), azobisisobutyronitrile (AIBN), benzoyl peroxide, 2,2-dimethoxy-2-phenylacetophenone, and one or more combinations thereof. In some embodiments, the photo-initiator may include one or more additional photosensitizers or co-initiators including for example one or more peroxides, aliphatic azo compounds and the like. In some embodiments, the catalyst, co-catalyst or accelerator; and the catalyst, co-catalyst or accelerator is an acrylate catalyst that promotes an acrylate polymerization reaction, or combinations thereof.

In some embodiments, the photo-initiator is CQ. The CQ may be used at a concentration of from about 0.01% to about 1%, from about 0.05% to about 0.75% from about 0.10% to about 0.5%, and any and all increments therebetween. In some embodiments the CQ is used at a concentration of 0.10%.

In an aspect, the bulk adhesive layer comprises one or more suitable dental resins. In some embodiments, the bulk adhesive layer comprises one or more methacrylates. In some embodiments, the bulk adhesive layer comprises catechol containing monomer, oligomer, or polymer. In some embodiments, the catechol containing monomer, oligomer, or polymer comprises PCS.

In an aspect, the bulk adhesive layer is a self-curing adhesive, wherein a catalyst is activated during application. In some embodiments, the bulk adhesive layer is a light-curing adhesive. In some embodiments, the bulk adhesive layer is a dual-curing adhesive that includes both self-curing and light-curing adhesives or adhesive properties. adhesive. In some embodiments, the bulk adhesive layer is a moisture-curing adhesive.

In an aspect, the disclosure is directed to the polymeric layer described herein disposed on a surface of the substrate. In some embodiments, the substrate comprises a substrate includes dental implants such as synthetic teeth having a ceramic surface or the like (e.g., zirconia or porcelain), tooth substrates (e.g., enamel, dentin or a combination of the two), fixed orthodontic devices including orthodontic brackets (e.g., titanium, stainless steel, gold, chrome, polypropylene or other suitable material), and/or ceramic restorative devices (e.g., zirconia crowns, etc.). In some embodiments, the substrate is wet, dry, semi-wet or moist.

In some embodiments, the substrate is a dental implant such as synthetic teeth having a ceramic surface or the like, for example zirconia or porcelain. In some embodiments, the substrate is a tooth substrate, for example, enamel, dentin or a combination of the two. In some embodiments, the substrate is one or more fixed orthodontic devices, for example one or more orthodontic brackets, or mounting post such as a titanium post for mounting an artificial tooth. In some embodiments, the one or more fixed orthodontic devices is an orthodontic bracket made of one or more suitable materials including for example, titanium, stainless steel, gold, chrome, polypropylene, PMMA or other suitable material. In some embodiments, the substrate is one or more ceramic restorative devices, for example a zirconia crown.

In some embodiments, the substrate is a polymeric compound. In some embodiments, the substrate is dentin. In some embodiments, the substrate is enamel. In some embodiments, the substrate is a ceramic, for example zirconia or porcelain. In some embodiments, the substrate is a metal, for example titanium.

In some embodiments, the substrate has a smooth surface. In some embodiments, the substrate has a rough surface. In some embodiments, the substrate has an even surface. In some embodiments, the substrate has an uneven surface.

In some embodiments, the substrate is wet. In some embodiments, the substrate is dry. In some embodiments, the substrate is semi-wet. In some embodiments, the substrate is moist.

In some embodiments, the substrate is a rigid substrate. In some embodiments, the substrate is a semi-rigid substrate. In some embodiments, the substrate is a flexible substrate.

In some embodiments, the adhesion strength is improved by including a catechol-containing polymer. For example, in some embodiments, such as that shown in FIG. 6, adhesion strength is improved when catechol-containing primer coating layer is applied to a substrate in combination with an adhesive layer as compared to adhesion strength of a substrate coated with adhesive alone.

In some embodiments, the adhesion durability is improved by including a catechol-containing polymer. For example, in some embodiments, such as that shown in FIG. 8, adhesion strength after a duration of time is improved when catechol-containing primer coating layer is applied to a substrate in combination with an adhesive layer as compared to a substrate coated with adhesive alone. In some embodiments, the adhesion strength is improved over adhesive alone for a duration of up to about 1 day, a duration ranging from about 1 day to about 7 days, from about 1 day to about 14 days, from about 7 days to about 28 days, from about 28 days to about 60 days, from about 30 days to about 90 days, from about 60 days to about 120 days, from about 90 days to about 180 days, from about 120 days to about 240 days, from about 180 days to about 360 days, from about 240 days to about 480 days, from about 360 days to about 720 days, and any and all increments therebetween.

In an aspect, the disclosure is directed to methods of coating a substrate comprising disposing the polymeric layer described herein on a surface of the substrate. In some embodiments the substrate is a dental substrate, including for example tooth substrates (e.g., enamel, dentin or a combination of the two), fixed orthodontic devices (e.g., orthodontic brackets), ceramic restorative devices (e.g., zirconia crowns), and the like. The coating may be applied to the dental substrate in situ. For example, the coating may be applied to an intact tooth inside the oral cavity of a subject. The coating may be applied ex vivo. For example, the coating may be applied to a dental device before being placed inside the oral cavity. The methods of disposing the polymeric layer described herein are not particularly limited and will be recognized by those skilled in the art.

In some embodiments, the methods of coating a substrate include disposing the polymeric layer on a substrate by spin coating, dip coating, spray coating, ink jet printing, or the like. In some embodiments, the methods comprise disposing the polymeric layer on a substrate by spin coating. In some embodiments, the methods comprise disposing the polymeric layer on a substrate by dip coating. In some embodiments, the methods comprise disposing the polymeric layer on a substrate by spray coating. In some embodiments, the methods comprise disposing the polymeric layer on a substrate by ink jet printing.

In some embodiments, the methods of coating a substrate comprise disposing the polymeric layer on a substrate, wherein the polymeric layer is applied to the substrate as a solution. In some embodiments, the solution comprises from about 0.001% by weight to about 10% by weight of the catechol containing monomer, polymer, or oligomer. In some embodiments, the solution comprises from about 0.01% by weight to about 5% by weight of the catechol containing monomer, polymer, or oligomer. In some embodiments, the solution comprises from about 0.01% by weight to about 1% by weight of the catechol containing monomer, polymer, or oligomer. In some embodiments, the solution comprises from about 0.1% by weight to about 1% by weight of the catechol containing monomer, polymer, or oligomer.

In some embodiments, the solution comprises from about 0.001% by weight to about 0.005% by weight of the catechol containing monomer, polymer, or oligomer; or from about 0.005% by weight to about 0.010% by weight of the catechol containing monomer, polymer, or oligomer; or from about 0.010% by weight to about 0.02% by weight of the catechol containing monomer, polymer, or oligomer; or from about 0.02% by weight to about 0.03% by weight of the catechol containing monomer, polymer, or oligomer; or from about 0.03% by weight to about 0.04% by weight of the catechol containing monomer, polymer, or oligomer; or from about 0.04% by weight to about 0.05% by weight of the catechol containing monomer, polymer, or oligomer; or from about 0.05% by weight to about 0.06% by weight of the catechol containing monomer, polymer, or oligomer; or from about 0.06% by weight to about 0.07% by weight of the catechol containing monomer, polymer, or oligomer; or from about 0.07% by weight to about 0.08% by weight of the catechol containing monomer, polymer, or oligomer; or from about 0.08% by weight to about 0.09% by weight of the catechol containing monomer, polymer, or oligomer; or from about 0.09% by weight to about 0.10% by weight of the catechol containing monomer, polymer, or oligomer; or from about 0.10% by weight to about 0.11% by weight of the catechol containing monomer, polymer, or oligomer; or from about 0.11% by weight to about 0.12% by weight of the catechol containing monomer, polymer, or oligomer; or from about 0.12% by weight to about 0.13% by weight of the catechol containing monomer, polymer, or oligomer; or from about 0.13% by weight to about 0.14% by weight of the catechol containing monomer, polymer, or oligomer; or from about 0.14% by weight to about 0.15% by weight of the catechol containing monomer, polymer, or oligomer; or from about 0.15% by weight to about 0.2% by weight of the catechol containing monomer, polymer, or oligomer; or from about 0.2% by weight to about 0.25% by weight of the catechol containing monomer, polymer, or oligomer; or from about 0.25% by weight to about 0.3% by weight of the catechol containing monomer, polymer, or oligomer; or from about 0.3% by weight to about 0.35% by weight of the catechol containing monomer, polymer, or oligomer; or from about 0.35% by weight to about 0.4% by weight of the catechol containing monomer, polymer, or oligomer; or from about 0.4% by weight to about 0.45% by weight of the catechol containing monomer, polymer, or oligomer; or from about 0.45% by weight to about 0.5% by weight of the catechol containing monomer, polymer, or oligomer; or from about 0.5% by weight to about 0.75% by weight of the catechol containing monomer, polymer, or oligomer; or from about 0.75% by weight to about 1% by weight of the catechol containing monomer, polymer, or oligomer; or from about 1.25% by weight to about 1.5% by weight of the catechol containing monomer, polymer, or oligomer; or from about 1.5% by weight to about 1.75% by weight of the catechol containing monomer, polymer, or oligomer; or from about 1.75% by weight to about 2% by weight of the catechol containing monomer, polymer, or oligomer.

In some embodiments, the catechol containing monomer, polymer, or oligomer used in the solution is poly-catechol styrene (PCS). In some embodiments, the solution comprises from about 0.001% by weight to about 10% by weight of PCS. In some embodiments, the solution comprises from about 0.01% by weight to about 5% by weight of PCS. In some embodiments, the solution comprises from about 0.01% by weight to about 1% by weight of PCS. In some embodiments, the solution comprises from about 0.1% by weight to about 1% by weight of PCS.

In some embodiments, the solution comprises from about 0.001% by weight to about 0.005% by weight of PCS; or from about 0.005% by weight to about 0.01% by weight of PCS; or from about 0.01% by weight to about 0.02% by weight of PCS; or from about 0.02% by weight to about 0.03% by weight of PCS; or from about 0.03% by weight to about 0.04% by weight of PCS; or from about 0.04% by weight to about 0.05% by weight of PCS; or from about 0.05% by weight to about 0.06% by weight of PCS; or from about 0.06% by weight to about 0.07% by weight of PCS; or from about 0.07% by weight to about 0.08% by weight of PCS; or from about 0.08% by weight to about 0.09% by weight of PCS; or from about 0.09% by weight to about 0.1% by weight of PCS; or from about 0.1% by weight to about 0.11% by weight of PCS; or from about 0.11% by weight to about 0.12% by weight of PCS; or from about 0.12% by weight to about 0.13% by weight of PCS; or from about 0.13% by weight to about 0.14% by weight of PCS; or from about 0.14% by weight to about 0.15% by weight of PCS; or from about 0.15% by weight to about 0.2% by weight of PCS; or from about 0.2% by weight to about 0.25% by weight of PCS; or from about 0.25% by weight to about 0.3% by weight of PCS; or from about 0.3% by weight to about 0.35% by weight of PCS; or from about 0.35% by weight to about 0.4% by weight of PCS; or from about 0.4% by weight to about 0.45% by weight of PCS; or from about 0.45% by weight to about 0.5% by weight of PCS; or from about 0.5% by weight to about 0.75% by weight of PCS; or from about 0.75% by weight to about 1% by weight of PCS; or from about 1.25% by weight to about 1.5% by weight of PCS; or from about 1.5% by weight to about 1.75% by weight of PCS; or from about 1.75% by weight to about 2% by weight of PCS.

In some embodiments, the solution also comprises an aqueous or organic solvent for dissolving the catechol containing monomer, polymer, or oligomer. In some embodiments, the organic solvent is acetone, tert-butyl alcohol, ethanol, isopropyl alcohol, or a combination thereof.

In some embodiments, the organic solvent is acetone. In some embodiments, the organic solvent is tert-butyl alcohol. In some embodiments, the organic solvent is ethanol. In some embodiments, the organic solvent is isopropyl alcohol. In some embodiments, the organic solvent is a combination of one or more of acetone tert-butyl alcohol, ethanol, isopropyl alcohol. In some embodiments, the organic solvent is acetone and the catechol or catechol containing material is PCS. In some embodiments, the organic solvent is tert-butyl alcohol and the catechol or catechol containing material is PCS. In some embodiments, the organic solvent is ethanol and the catechol or catechol containing material is PCS. In some embodiments, the organic solvent is isopropyl alcohol and the catechol or catechol containing material is PCS. In some embodiments, the organic solvent is a combination of one or more of acetone tert-butyl alcohol, ethanol, isopropyl alcohol, and the catechol or catechol containing material is PCS. In some embodiments, the organic solvent further comprises one or more oxidizing agents or acidifying agents. For example, in some embodiments the organic solvent further comprises acetic acid.

The pH of the solution is not particularly limited. In some embodiments, the pH of the solution is about 3; or about 3.5; or about 4; or about 4.5; or about 5; or about 5.5; or about 6; or about 6.5; or about 7; or about 7.5; or about 8; or about 8.5; or about 9; or about 9.5; or about 10; or about 10.5; or about 11.

In some embodiments, the pH of the solution is from about 3-3.5; or about 3.5-4; or about 4-4.5; or about 4.5-5; or about 5-5.5; or about 5.5-6; or about 6-6.5; or about 6.5-7; or about 7-7.5; or about 7.5-8; or about 8-8.5; or about 8.5-9; or about 9-9.5; or about 9.5-10; or about 10-10.5; or about 10.5-11.

In some embodiments, the methods of coating a substrate comprise disposing the polymeric layer on a substrate, wherein the substrate comprises a polymeric compound, dentin, enamel, a ceramic, a metal, or combinations thereof; and wherein the substrate is wet, dry, semi-wet or moist. In some embodiments, the methods of coating a substrate comprise within the oral cavity of a subject.

In some embodiments, the methods of coating a substrate comprise disposing the polymeric layer on a substrate comprising a polymeric compound. In some embodiments, the methods comprise disposing the polymeric layer on a substrate comprising dentin. In some embodiments, the methods comprise disposing the polymeric layer on a substrate comprising enamel. In some embodiments, the methods comprise disposing the polymeric layer on a substrate comprising a ceramic, for example zirconia or porcelain. In some embodiments, the methods comprise disposing the polymeric layer on a substrate comprising a metal, for example titanium, stainless steel, gold, chrome, or other suitable metal. In some embodiments, the methods comprise disposing the polymeric layer on a substrate comprising poly (methyl methacrylate) (PMMA), polypropylene, or other suitable plastic.

In some embodiments, the methods of coating a substrate comprise disposing the polymeric layer on a wet substrate. In some embodiments, the methods comprise disposing the polymeric layer on a dry substrate. In some embodiments, the methods comprise disposing the polymeric layer on a semi-wet substrate. In some embodiments, the methods comprise disposing the polymeric layer on a moist substrate.

In some embodiments, the methods of coating a substrate comprise disposing the polymeric layer on a substrate in a dry environment. In some embodiments, the methods comprise disposing the polymeric layer on a substrate in an ambient environment. In some embodiments, the methods comprise disposing the polymeric layer on a substrate in a humid environment. In some embodiments, the methods comprise disposing the polymeric layer on a substrate in an aqueous environment. In some embodiments, the environment includes the oral cavity of a subject.

In some embodiments, the methods of making a substrate comprise disposing the polymeric layer on a substrate as a continuous layer. In some embodiments, the methods of making a substrate comprise disposing the polymeric layer on a substrate as a non-continuous layer. In some embodiments, the methods of making a substrate comprise disposing the polymeric layer on a substrate as a patterned layer or a textured layer.

In some embodiments, the methods of coating a substrate comprise disposing the polymeric layer on a substrate by spin coating, dip coating, spray coating, flood coating, brushing, wiping, or the like. In some embodiments, the methods comprise disposing the polymeric layer on a substrate by spin coating. In some embodiments, the methods comprise disposing the polymeric layer on a substrate by dip coating. In some embodiments, the methods comprise disposing the polymeric layer on a substrate by spray coating. In some embodiments, the methods comprise disposing the polymeric layer on a substrate by ink jet printing. In some embodiments, the methods comprise disposing the polymeric layer on a substrate by flood coating. In some embodiments, the methods comprise disposing the polymeric layer on a substrate by brushing. In some embodiments, the methods comprise disposing the polymeric layer on a substrate by wiping.

In an aspect, the disclosure is directed to methods of making a substrate comprising disposing the polymeric layer described herein on a surface of the substrate, and further comprising disposing a bulk adhesive layer on the polymeric layer. The methods of disposing the bulk adhesive layer described herein are not particularly limited and will be recognized by those skilled in the art.

In some embodiments, the methods of making a substrate comprise disposing the bulk adhesive layer on the polymeric layer by spin coating, dip coating, spray coating, ink jet printing, flood coating, brushing, wiping, or the like. In some embodiments, the methods comprise disposing the bulk adhesive layer on the polymeric layer by spin coating. In some embodiments, the methods comprise disposing the bulk adhesive layer on the polymeric layer by dip coating. In some embodiments, the methods comprise disposing the bulk adhesive layer on the polymeric layer by spray coating. In some embodiments, the methods comprise disposing the bulk adhesive layer on the polymeric layer by ink jet printing. In some embodiments, the methods comprise disposing the bulk adhesive layer on the polymeric layer by flood coating. In some embodiments, the methods comprise disposing the bulk adhesive layer on the polymeric layer by brushing. In some embodiments, the methods comprise disposing the bulk adhesive layer on the polymeric layer by wiping.

In some embodiments, the methods of making a substrate comprise disposing the bulk adhesive layer on the polymeric layer in a dry environment. In some embodiments, the methods comprise disposing the bulk adhesive layer on the polymeric layer in an ambient environment. In some embodiments, the methods comprise disposing the bulk adhesive layer on the polymeric layer in a humid environment, for example inside the oral cavity of a subject. In some embodiments, the methods comprise disposing the bulk adhesive layer on the polymeric layer in an aqueous environment.

In some embodiments, the methods of making a substrate comprise disposing the bulk adhesive layer on the polymeric layer on a substrate as a continuous layer. In some embodiments, the methods comprise disposing the bulk adhesive layer on the polymeric layer as a non-continuous layer. In some embodiments, the methods comprise disposing the bulk adhesive layer on the polymeric layer as a patterned layer or a textured layer.

In some embodiments, the methods for disposing the bulk adhesive layer as a non-continuous layer or for disposing the polymeric layer as a non-continuous layer comprise disposing the layers in an ordered pattern or a stochastic pattern.

In some embodiments, the ordered pattern comprises strips, a grid, concentric circles or a dot pattern. In some embodiments, the methods comprise disposing the bulk adhesive layer and/or the polymeric layer as strips. In some embodiments, the methods comprise disposing the bulk adhesive layer and/or the polymeric layer as a grid. In some embodiments, the methods comprise disposing the bulk adhesive layer and/or the polymeric layer as concentric circles. In some embodiments, the methods comprise disposing the bulk adhesive layer and/or the polymeric layer as a dot pattern.

In some embodiments, the methods comprise disposing the bulk adhesive layer and/or the polymeric layer stochastically.

The bulk adhesive layer and/or the polymeric layer can be disposed in particular shapes or in an amorphous manner. In some embodiments, the methods comprise disposing the bulk adhesive layer and/or the polymeric layer as a dot, a circle, a square, a rectangle, a pentagon, a hexagon; or as amorphous.

In an embodiment, the bulk adhesive layer and/or the polymeric layer are shaped as a dot. In an embodiment, the bulk adhesive layer and/or the polymeric layer are shaped as a circle. In an embodiment, the bulk adhesive layer and/or the polymeric layer are shaped as an oval. In an embodiment, the bulk adhesive layer and/or the polymeric layer are shaped as a triangle. In an embodiment, the bulk adhesive layer and/or the polymeric layer are shaped as a square. In an embodiment, the bulk adhesive layer and/or the polymeric layer are shaped as a rectangle. In an embodiment, the bulk adhesive layer and/or the polymeric layer are shaped as a pentagon. In an embodiment, the bulk adhesive layer and/or the polymeric layer are shaped as a hexagon. In an embodiment, the bulk adhesive layer and/or the polymeric layer are amorphous.

In some embodiments, the methods comprise disposing the bulk adhesive layer and/or the polymeric layer as gridlines, criss-cross lines, random lines, concentric circles, eccentric circles, spaghetti patterns and flat strips.

In an embodiment, the bulk adhesive layer and/or the polymeric layer are shaped as gridlines. In an embodiment, the bulk adhesive layer and/or the polymeric layer are shaped as criss-cross lines. In an embodiment, the bulk adhesive layer and/or the polymeric layer are shaped as random lines. In an embodiment, the bulk adhesive layer and/or the polymeric layer are shaped as concentric circles. In an embodiment, the bulk adhesive layer and/or the polymeric layer are shaped as eccentric circles. In an embodiment, the bulk adhesive layer and/or the polymeric layer are shaped as a spaghetti pattern. In an embodiment, the bulk adhesive layer and/or the polymeric layer are shaped as a flat strip.

In an aspect, the disclosure is directed to a layered structure comprising the polymeric layer described herein. In some embodiments, layered structure comprises multiple polymeric layers described herein. In some embodiments, layered structure comprises two polymeric layers described herein. In some embodiments, layered structure comprises three polymeric layers described herein. In some embodiments, layered structure comprises four polymeric layers described herein. In some embodiments, layered structure comprises five polymeric layers described herein.

In an aspect, the disclosure is directed to a layered structure comprising the polymeric layer described herein disposed adjacent to and in contact with a bulk adhesive layer.

In some embodiments, layered structure comprises multiple bulk adhesive layers described herein. In some embodiments, layered structure comprises two bulk adhesive layers described herein. In some embodiments, layered structure comprises three bulk adhesive layers described herein. In some embodiments, layered structure comprises four bulk adhesive layers described herein. In some embodiments, layered structure comprises five bulk adhesive layers described herein.

The following Examples are provided to illustrate some of the concepts described within this disclosure. While the Examples are considered to provide embodiments, it should not be considered to limit the more general embodiments described herein.

EXAMPLES

Example 1—PCS Priming Enamel Promotes Dental Bracket Bonding with a Dental Acrylic Some embodiments of the present invention as contemplated herein relate to a process of enhancing the bonding of a fixed orthodontic device, a composite resin, or a ceramic restoration material to a dental surface, such as enamel or dentin. This bonding is done using an adhesive such as an acrylic adhesive, and a primer layer such as a PCS. This primer layer may contain other chemical components, such as a catalyst, co-catalyst or an accelerator. In order to evaluate the effect of a PCS primer layer on bonding strength, the failure force of a dental bracket adhered using an acrylic dental adhesive was tested.

Materials

CUSP-LOK™ I dental brackets (Xemax; Pasadena, CA) were used to adhere to a tooth structure for testing. Briefly, non-carious extracted molars (17 years<age<33 years) were obtained, cleaned, and stored at 4° C. in chloramine T prior to use. The bracket was composed of a ¾ inch 14 k gold chain attached to a stainless steel orthodontic bracket. The bracket had a surface 3 mm by 4 mm bonding area.

The bracket was adhered to the tooth using a NATURAL ELEGANCE® Universal One (Henry Schein, Inc.; Melville, NY) dental adhesive. This is a light-cure, self-etch (pH 2.8) bisphenol A glycidyl methacrylate (bis-GMA) adhesive. A dark blue etchant gel (40% phosphoric acid) (Henry Schein, Inc.; Melville, NY) was used and the adhesive was cured using a 5 W LED Cure Light Lamp (ORILAO®; China).

A two-part epoxy-based resin from Amazing Casting Resin (ALUMILITE™; Galesburg, MI) was used to embed the tooth for mounting into the testing apparatus.

A 22-gauge copper wire (Hillman Group; Cincinnati, OH) was mounted onto the dental bracket.

The tooth mounted tooth was primed using a PCS primer. The primer used was a 0.1% solution of PCS polymer diluted in acetone. PCS was synthesized in the laboratory of Professor Jon Wilker (Purdue University) using established synthetic approaches.

The bond strength measurements were performed using a bond strength tester. Instru-Met Model 15k Pounds (Instru-Met; Union, New Jersey.). This device was equipped with a 10-Pound Tension Load Cell (INSTRON®; Norwood, MA).

Adhesion to Zirconia

Methods

KATANA™ Zirconia STML specimens were sectioned, sintered, and embedded in acrylic resin. Specimen surfaces were finished with 600 grit silicon carbide abrasive with cooling water, and air-particle abraded with 50 μm aluminum oxide. A total of 100 (n=25) samples were prepared and split into four study groups, the first two acting as the controls: ceramic primer (CLEARFI™ Ceramic Primer Plus) on dry surface, ceramic primer on wet surface, experimental primer on dry surface, and experimental primer on wet surface. After primer applications of 10 seconds, the surfaces were air-sprayed, micro brushed with bonding agent (OPTIBOND™ Solo Plus), and light cured for 20 seconds. Cylindrical composite samples (2.1 mm diameter, 3 mm height) were bonded to the zirconia surfaces by packing the material into cylindrical shaped plastic matrices and curing with a light cure for 40 seconds. The specimens were stored for 48 hours at room temperature (24° C.) and then mounted in a universal testing machine. SBS was determined at a crosshead speed of 0.5 mm/min and expressed in MPa. ANOVA and Pairwise comparison with Tukey tests were used for statistical analysis.

Results

Figure 7:
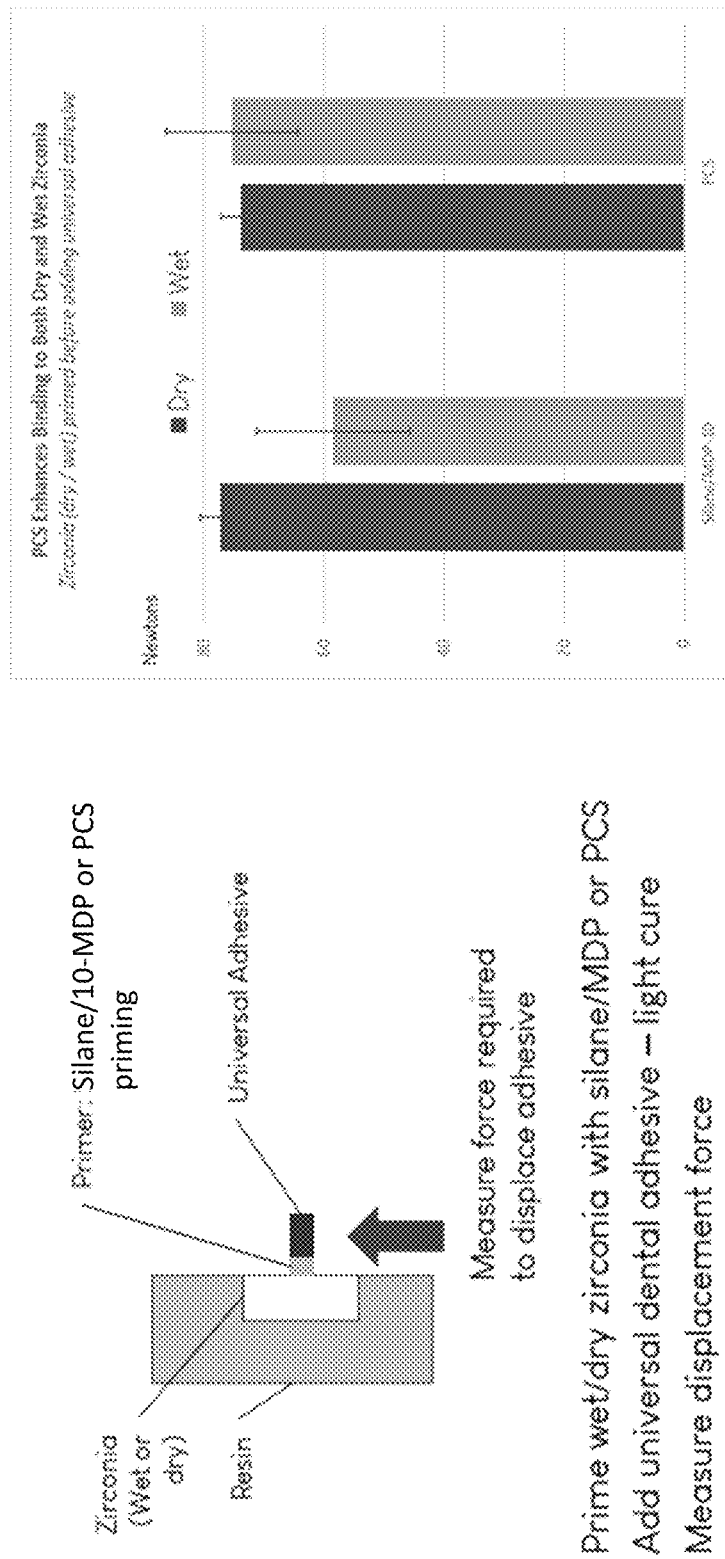
FIG. 7 demonstrates that PCS priming enhances the adhesion strength to wet zirconia. A dental adhesive was applied to samples of zirconia, either dry or pre-wetted, after priming with PCS or a silane-based/10-Methacryloyloxydecyl dihydrogen phosphate (10-MDP) containing dental primer. The left panel depicts a schematic of the experimental setup. The right panel depicts results demonstrating that PCS priming improves binding to wet ceramic surfaces.

Mean SBS values were 33.6 MPa and 25.4 MPa for the dry and wet control groups, respectively. Mean SBS values were 32.1 MPa and 32.7 MPa for the dry and wet experimental groups, respectively. While the results for the dry groups were not different (p>0.05), there was a statistically significant difference in the results between the wet experimental and control groups (p<0.05). As shown in FIG. 7, wet surfaces did not change bonding performance of experimental primer.

CONCLUSION

The pre-treatment of zirconia surfaces with a mussel-biomimetic primer may improve the bond strength to the surfaces in wet surface conditions.

Example 2—Priming Dentin with PCS Enhances Durability of Acrylic Bonding

In order to test the hypothesis that PCS priming might not only have the ability to enhance initial bond strength it might also be able to enhance the durability of the acrylic/dentin bond, bond durability to dentin was tested using a micro-mechanical fatigue test as has been described previously. Without being bound to theory, it was hypothesized that oxidized catechol moieties (quinones) are capable of covalently bonding to exposed collagen via a Schiff base or Michael addition to free —NH2 and —SH groups (Guvendiren et al, 2009.; LaVoie et al, 2005.; Burzio et al, 2000.).

Materials

Non-carious extracted molars (17 years<age<33 years) were obtained, sectioned, and dentin blocks were cut into 2×2×2 mm$^3$ fragments. A caulk from DENTSPLY SIRONA® (York, PA), which is a 34% phosphoric acid gel was used for etching the dentin. A combined total-etch, self-etch and selective-etch adhesive primer-adhesive from SCOTCHBOND® Universal Adhesive (3M®; Saint Paul, MN) was used. G-xnial SCULPT™ (Tokyo, Japan) composite, which is a light-cured, universal nano-hybrid, compactable composite resin material used for fillings was used as the composite.

Methods

The effectiveness of PCS priming on dental adhesive bonding to dentin was evaluated using a resin-dentin interface fatigue test as described by Mutluay et al. 2013. Briefly, the process included acid etching the dentin blocks for 15 seconds, followed by rinsing with water and air drying. PCS (0.1% in acetone) was then brushed onto the dentin bonding surface and allowed to air dry for 10 seconds. SCOTCHBOND® (primer+adhesive combination from 3M®; Saint Paul, MN) was then added and light-cured for 15 seconds. The G-xnial SCULPT™ composite material was then added and light-cured for 30 seconds. Samples were then submerged in water for 24 hours, and the first bond strength readings taken. The remaining samples were then incubated in HBSS (Hanks' Balanced Solution) at 37 C for aging. After 10 days of incubation, the bond strength reading was assessed again.

Results

Figure 8:
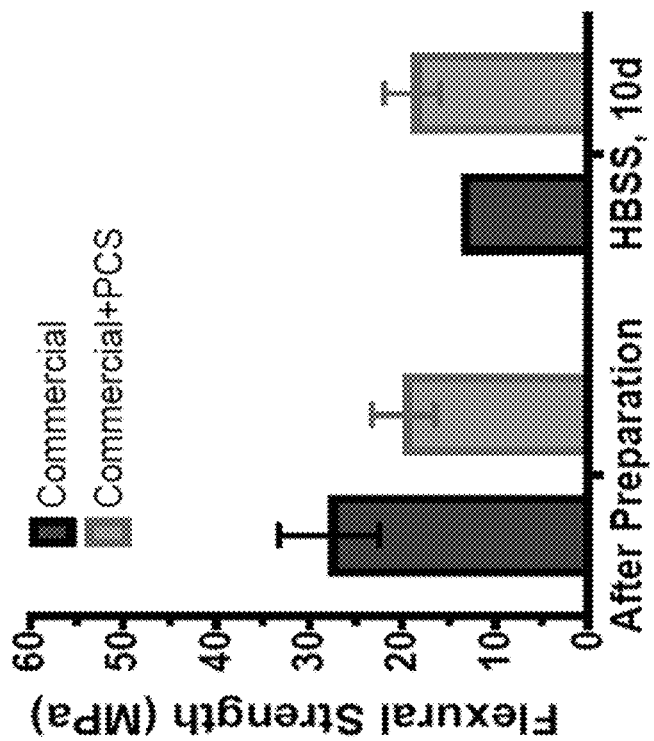
FIG. 8 shows results demonstrating that PCS priming provides long-term bonding to dentin. The panel on the left depicts a schematic of the how the adhesive is applied. Wet or dry zirconia was primed with silane/MDP or PCS. A universal dental adhesive was then applied, and light cured. The displacement force was then measured. The panel on the right depicts flexural strength. PCS improves strength when applied to wet zirconia.
Figure 8:
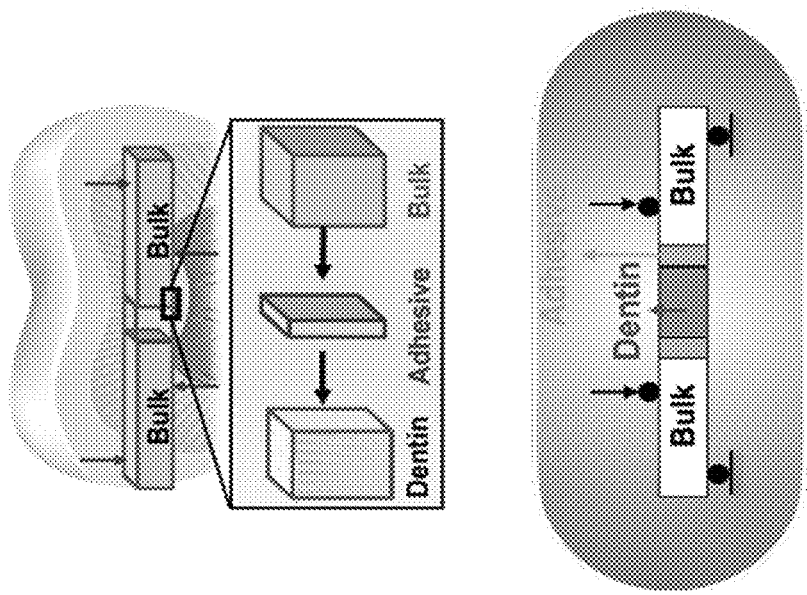

While the bond strength of the control samples dropped significantly (~40%) over the assay period, shown in FIG. 8, PCS-primed samples displayed virtually no loss of strength over the 10-day aging period. The PCS-primed sample was initially lower in strength than the control. This is likely due to incomplete polymerization due to PCS inhibiting polymerization of the acrylic adhesive due to catechol scavenging of free-radicals.

Example 3—PCS as a Primer with a Photoinitiator Additive is a Bonding Promotor of a Dental Acrylic on a Dentin Surface In order to evaluate the effect of using photoinitiator additive in the PCS primer, bond strength measurements were conducted. Flat bonding sites were prepared on buccal surfaces of extracted human teeth by grinding the teeth on a water-cooled abrasive wheel (ECOMET III™ Grinder, Ltd.) to a 600-grit surface to expose dentin. Each test group was performed with 12-15 teeth.

Each adhesive treatment was then applied to the dentin following acid conditioning, rinsing, and blot drying to avoid desiccation. First, primer solution was added to the dentin and allowed to dry briefly in air. The priming solution was 0.1 w/w % PCS in acetone. In one set of samples, a photo-crosslinking agent was added to the primer. For example, camphorquinone (CA) and a tertiary amine co-initiator was used.

Bonded assemblies were formed using an ULTRADENT™ Shear Bond test apparatus creating a cylinder 2.37 mm in diameter. After extrusion into the Teflon former, composite material specimens were light polymerized for 30 seconds using a VALO™ Grand LED curing light. The specimen was then removed from the specimen mold, and samples were allowed to cure for 24 hours before shear testing. For shear testing, bonded assemblies were placed in an MTS INSIGHT™ test frame equipped with an ULTRADENT™ notched chisel. The specimens were then aligned with the shaped chisel against and parallel to the bonding sites. Each cylinder was placed under continuous loading at 1 mm per minute until fracture occurred. Shear bond strength was reported in MPa.

Figure 10:
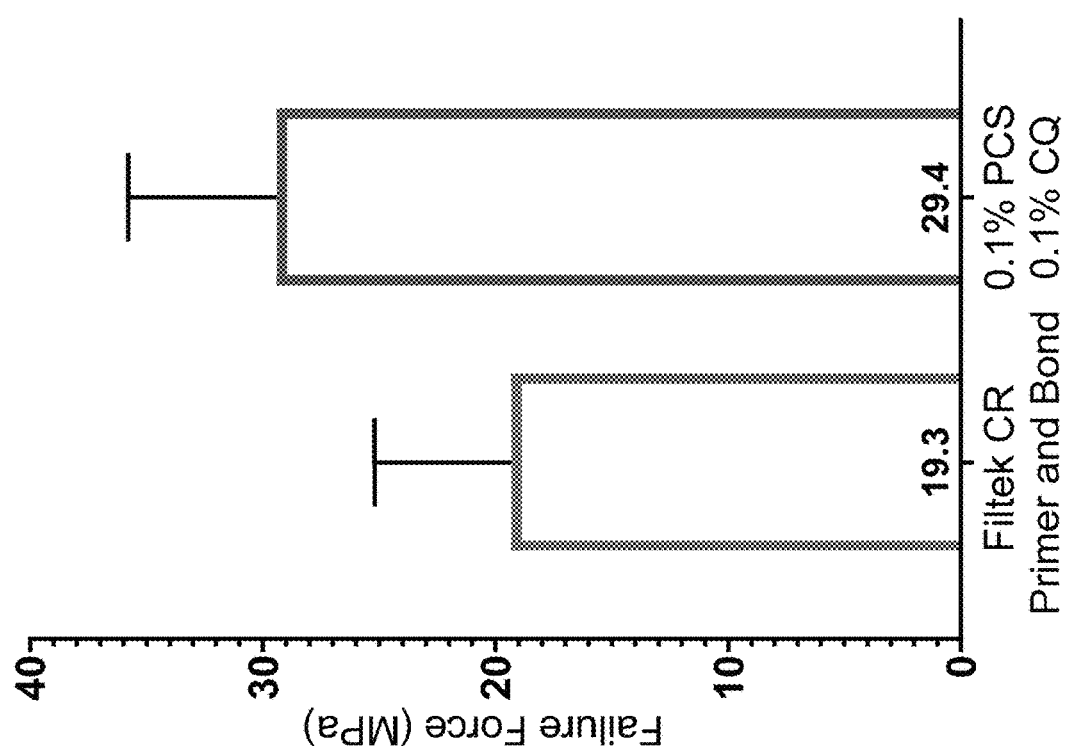
FIG. 10 depicts bond strength data using PCS as a primer with a photoinitiator additive as a bonding promotor of a dental acrylic on a dentin surface. Results show a 0.1% PCS primer layer with 0.1% camphorquinone (CQ) photoinitiator additive is sufficient to improve and promote bonding of a dental acrylic, FILTEK® CR, to the dentin surface. Samples were allowed to cure for 24 hours before shear testing. Error bars are standard deviation.

Results shown in FIG. 10 indicate including a photoinitiator with the PCS primer provide an increase bond strength.

In order to evaluate the conversion of urethane dimethacrylate (UDMA), percent UDMA conversion with photoinitiator was measured in the presence of increasing concentrations of PCS.

Figure 9:
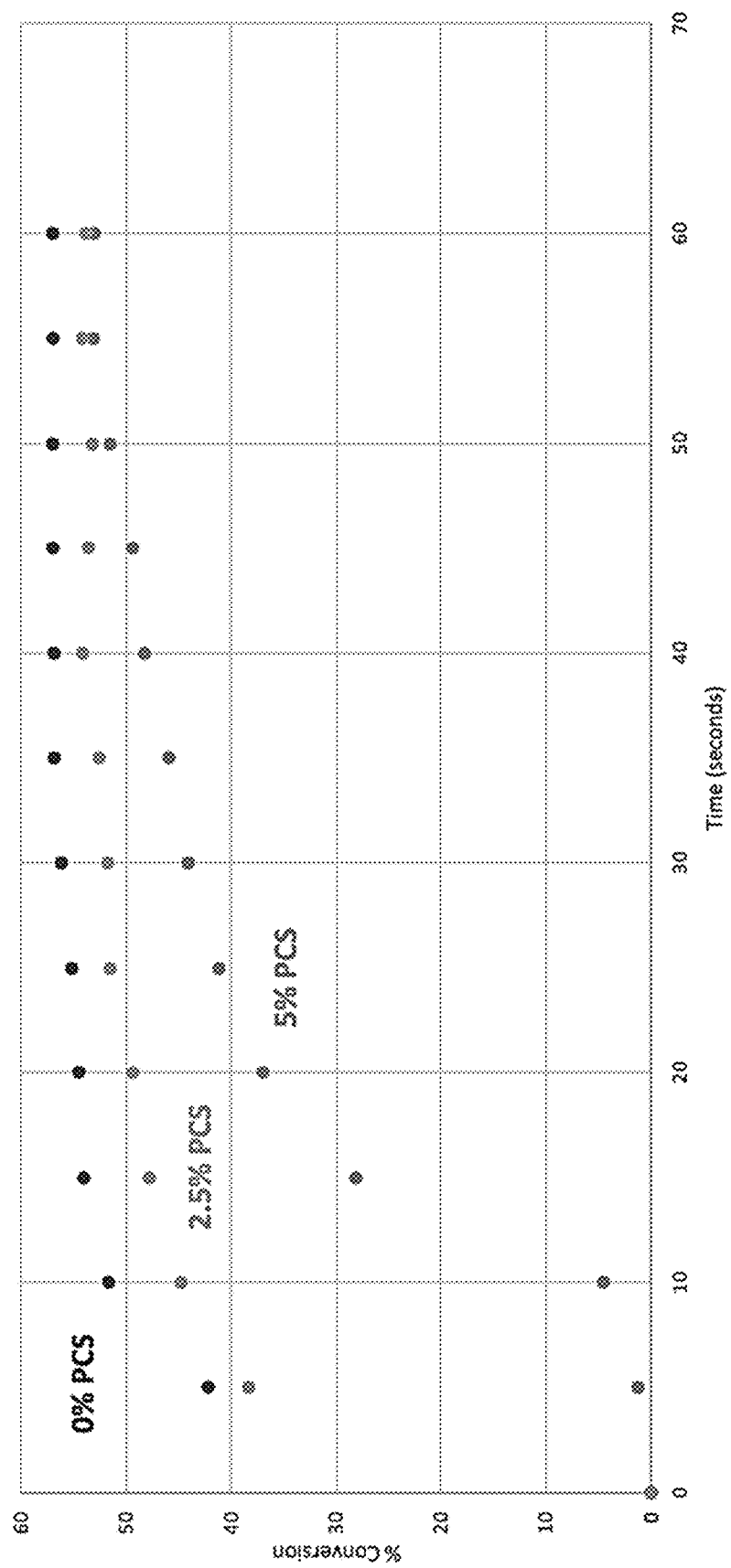
FIG. 9 shows the conversion of UDMA in the presence of PCS. Percent conversion of UDMA with 0.5 w/w % camphorquinone/coinitiator was measured over time using FTIR-ATR. Formulations with different concentrations of PCS were irradiated in situ on the ATR crystal.

To evaluate UDMA (urethane dimethacrylate) conversion, camphorquinone (CQ) consumption in methacrylate resins using 0.5 w/w % CQ was measured over time. Briefly, UDMA was mixed and CQ was used as the visible light photosensitizer. Resins were photoactivated with a dental light source and percentage conversion was assessed in the sample specimens using Fourier transform infrared spectroscopy—attenuated total reflectance (FTIR-ATR). Results shown in FIG. 9 indicate a reduction in the percentage conversion with increasing amounts of PCS.

Example 4—Reduction of Bulk PCS Increases Bonding to Aluminum

To determine if oxidized functional groups (quinones) in PCS are responsible for the enhanced durability of the dentin bond, the effect of acid treatment on PCS bonding to a metal surface was evaluated. Since quinone binds poorly to metal, and catechol bonds strongly, the conversion of quinones to catechol with acid was evaluated to determine if an increased bonding strength to metal would be achieved.

Figure 11:
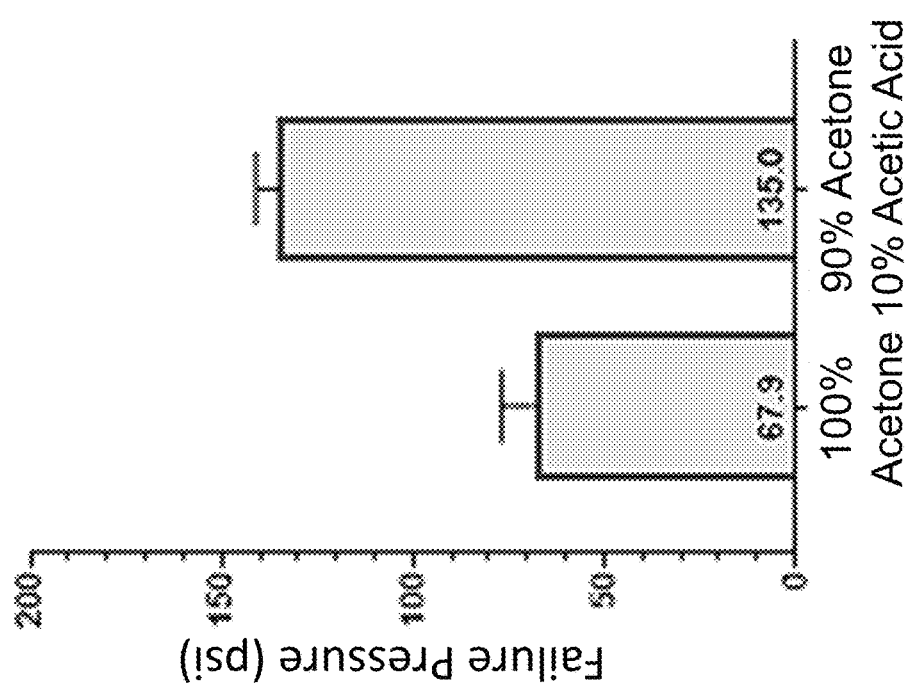
FIG. 11 shows that a reduction of bulk PCS increases bonding to aluminum. PCS was dissolved in 100% acetone or 90% acetone and 10% acetic acid. Acidification markedly increased bond strength. Error bars are standard error of the mean.

Briefly, aluminum samples were bonded with 80% bulk PCS. The solvent used was either 100% acetone, or 90% acetone and 10% acetic acid. A 10% glacial acetic acid solution was used in order to evaluate whether the acid would promote the reduction of quinone to hydroxyl groups. The samples were left to sit unclamped for one hour at room temperature, kept in an oven at 55° C. for 22 hours, allowed to cool for one hour at room temperature, and then tensile strength tested. Results are shown in FIG. 11. Error bars represent standard error of the mean.

A consistent increase in bonding strength to metal in the presence of an acid was observed, suggesting that the PCS was partially oxidized into quinones. These quinones were shown to promote durable, covalent bonding to dentin.

Example 5. Sample Preparation Optimization

Figure 12:
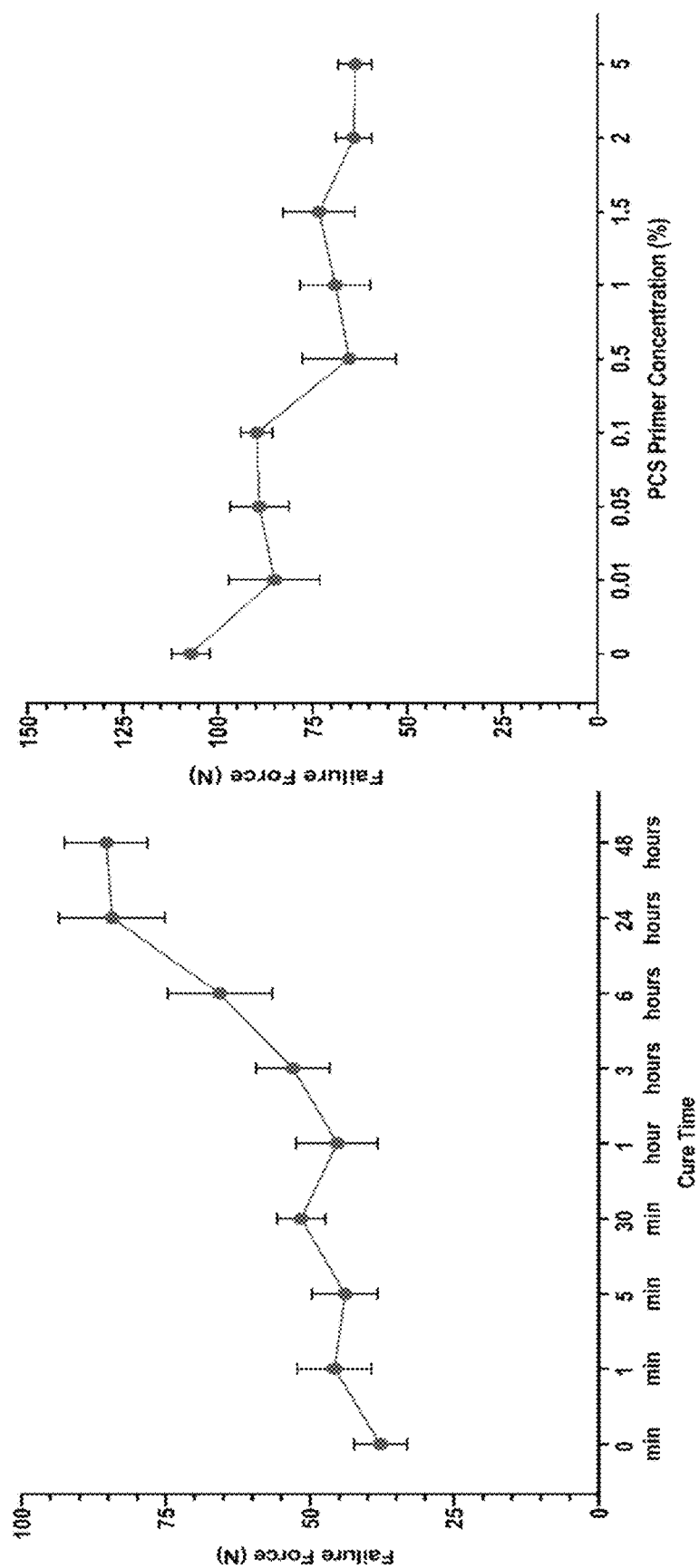
FIG. 12 shows that dental acrylic is fully polymerized after 48 hours when using 0.1% PCS primer as a bonding promotor. The left panel demonstrates optimal cure time for a dental acrylic, Clearfil SE Bond, to fully polymerize with PCS as a bonding promotor is 48 hours. Shear testing samples following 48 hours were conducted and demonstrate that the bond was fully cured and remained stable for at least 24 hours. The right panel demonstrates optimal percentage PCS was about 0.1% in acetone. Samples were cured in dry conditions. Error bars represent standard error of the mean.

In order to determine the optimal curing time, failure force of samples prepared as previously described with 0.1% PCS primer were subjected the bond strength testing at increasing time increments to 48 hours. Results shown in FIG. 12 indicate that maximum bond strength is achieved at 24 hours of cure time and maintained to 48 hours.

In addition, the optimal percentage of PCS primer concentration was evaluated by measuring bond strength with increasing concentrations of PCS. Results shown in FIG. 12 also indicate maximum bond strength was achieved at about 0.01% to about 0.1% PCS, and most consistently at 0.1% PCS in acetone. Accordingly, 0.1% PCS in acetone or other suitable solvent was used in the experiments presented herein.

What is claimed:

1. A polymeric layer comprising a catechol-containing thin-film comprised of a polymer containing catechol, semi-quinone, or quinone to enhance the binding strength of a dental adhesive;
wherein the polymeric layer comprises the reactive species separate from the catechol or catechol containing material; and the reactive species comprises an acrylic, a silane, a silicone, a methacrylate, a polyvinyl alcohol (PVA) or a combination thereof;
wherein the acrylic comprises an acrylic such as 2,2-bis [4-(2-hydroxy-3-methacryloyloxypropoxy)phenyl]propane (BisGMA), ethoxylated bisphenol-A dimethacrylate (EBPADMA), triethylene glycol dimethacrylate (TEGDMA), urethane dimethacrylate, (UDMA), tert-butylphenoxy BisGMA (MtBDMA), modified urethane dimethacrylate, amide modified bisphenol-A, $CH_3$BisGMA, acidic bisphenol-A dimethacrylate, dimethacrylate from cycloaliphatic epoxide, aromatic urethane dimethacrylate, urethane modified BisGMA, acid aromatic dimethacrylate, oxydiphthalic-acid dimethacrylate, phenyl dihydroxymethacrylate diphosphonate, Acidic Bisphenol-A dimethacrylate, morpholine carbonyl methacrylate, phenyl carbonate methacrylate.

2. The polymeric layer of claim 1, wherein the catechol-containing thin-film comprises monomeric, oligomeric, or polymeric catechol or catechol containing material, wherein said catechol presents as a catechol and/or as a semi-quinone and/or as a quinone without the presence of an amine; and wherein the polymeric layer optionally comprises at least one of: a) a reactive species separate from the catechol or catechol containing material; and b) a catalyst, co-catalyst or an accelerator.

3. The polymeric layer of claim 1 further comprising free radical polymerization initiators such as acrylate polymerization initiators, including those that are light activated, such as benzoyl peroxide (BPO), 2,3-bornanedione (Camphorquinone), Ethyl-4-(dimethylamino)benzoate (EDMAB), 2-(Ethylhexyl)-4-(dimethylamino)benzoate (ODMAB), 2-(Ethylhexyl)-4-(dimethylamino)benzoate (TPO), Diphenyl(2,4,6-trimethylbenzoyl)-phosphineoxide or combinations thereof.

4. The polymeric layer of claim 1, wherein the reactive species is the acrylate.

5. The polymeric layer of claim 1, wherein the polymeric layer is disposed upon a dental substrate.

6. The polymeric layer of claim 5, wherein the dental substrate comprises one or more of a ceramic, a polymer, a composite and a metal.

7. The polymeric layer of claim 6, wherein: the ceramic comprises zirconia or porcelain; the polymer comprises acrylic, polypropylene, poly(methyl methacrylate), or one or more combinations thereof; the composite comprises one or more of enamel, dentin, or combinations thereof; and the metal comprises one or more of titanium, stainless steel, gold, chrome, or one or more combinations thereof.

8. The polymeric layer of claim 1, wherein the polymeric layer comprises one or more of a primer layer, an adhesive layer, or a layered restoration.

9. The polymeric layer of claim 1, wherein the polymeric layer has a thickness of from about 10 nanometers to about 500 microns.

10. The polymeric layer of claim 1, wherein the catechol or catechol-containing material comprises poly-catechol styrene (PCS).

11. The polymeric layer of claim 10, wherein the PCS comprises a 0.1% solution of PCS.

12. The polymeric layer of claim 1 further comprising one or more photo-initiators comprising one or more of camphorquinone (CQ), azobisisobutyronitrile (AIBN), benzoyl peroxide, 2,2-dimethoxy-2-phenylacetophenone, and one or more combinations thereof.

13. The polymeric layer of claim 1, wherein the binding longevity of the dental adhesive is improved over dental adhesives not containing a catechol-containing material.

14. A method of coating a substrate comprising disposing the polymeric layer of claim 1 on a surface of the substrate.

15. The method of claim 14, wherein the substrate comprises a dental substrate comprising one or more of a ceramic, a polymer, a composite and a metal, wherein: the ceramic comprises zirconia or porcelain; the polymer comprises acrylic, polypropylene, poly (methyl methacrylate), or one or more combinations thereof; the composite comprises one or more of enamel, dentin, or combinations thereof; and the metal comprises one or more of titanium, stainless steel, gold, chrome, or one or more combinations thereof.

16. The method of claim 14, wherein the substrate is wet, dry, semi-wet or moist.

17. The method of claim 16, wherein the substrate is inside the oral cavity of a subject.

18. The method of claim 14, wherein the binding longevity of the dental adhesive is improved over dental adhesives not containing a catechol-containing material.

* * * * *